United States Patent [19]

Courty et al.

[11] Patent Number: 4,552,861

[45] Date of Patent: Nov. 12, 1985

[54] PROCESS FOR MANUFACTURING CATALYSTS CONTAINING COPPER, ZINC, ALUMINUM AND AT LEAST ONE METAL FROM THE GROUP FORMED OF RARE EARTHS AND ZIRCONIUM AND THE RESULTANT CATALYSTS FOR REACTIONS INVOLVING A SYNTHESIS GAS

[75] Inventors: Philippe Courty, Houilles; Daniel Durand, Rueil Malmaison; Christine Travers, Rueil Malmaison; Patrick Chaumette, Rueil Malmaison; Alain Forestiere, Vernaison, all of France

[73] Assignee: Institut Francais du Petrole, Rueil-Malmaison, France

[21] Appl. No.: 707,128

[22] Filed: Mar. 1, 1985

[30] Foreign Application Priority Data

Mar. 2, 1984 [FR] France ............................. 84 03325

[51] Int. Cl.$^4$ .................. B01J 21/04; B01J 23/06; B01J 23/10; B01J 23/72
[52] U.S. Cl. .................................. 502/302; 502/303; 502/304; 502/329; 502/342
[58] Field of Search ............... 502/302, 303, 304, 329, 502/342

[56] References Cited

U.S. PATENT DOCUMENTS 3,758,417  9/1973  Magoon et al. ..................... 502/303
4,257,920  3/1981  Sugier et al. ........................ 502/302
4,279,781  7/1981  Dienes et al. ....................... 502/343

Primary Examiner—W. J. Shine
Attorney, Agent, or Firm—Millen & White

[57] ABSTRACT

Manufacture of catalysts containing at least four essential metals: copper, zinc, aluminum and at least one metal selected from the group formed of rare earths and zirconium.

The process comprises the formation of a crystallized precipitate of the above-mentioned metals by intimate mixture of a crystallized precipitate of copper, zinc and aluminum, containing less than 0.06% by weight of sodium after washing, with a precipitate of at least one metal of the rare earths group and/or zirconium, containing less than 3% of nitrogen after washing.

The catalysts are used in balanced reactions involving alcohols and synthesis gases, and particularly for methanol synthesis.

22 Claims, No Drawings

PROCESS FOR MANUFACTURING CATALYSTS CONTAINING COPPER, ZINC, ALUMINUM AND AT LEAST ONE METAL FROM THE GROUP FORMED OF RARE EARTHS AND ZIRCONIUM AND THE RESULTANT CATALYSTS FOR REACTIONS INVOLVING A SYNTHESIS GAS

This invention concerns a process for manufacturing a catalyst, essentially of homogeneous composition, highly active, stable and selective, useful in processes involving a balanced reaction of carbon oxides (CO, $CO_2$) with hydrogen, particularly for producing methanol from synthesis gas and in reactions of decomposing primary alcohols and particularly methanol to a mixture containing carbon oxides and hydrogen.

These catalysts comprise at least four metals: copper, aluminum, zinc and at least one metal from the group of rare earths having atomic numbers from 57 to 71 included and/or zirconium. They may optionally further contain 0.01–1% of at least one metal selected from the group consisting of palladium, rhenium and platinum. They may also contain, in addition, 0.5–5% of silver.

BACKGROUND OF THE INVENTION

The catalysts with a base of copper and zinc oxides have been known since many years; they have been disclosed as early as 1933 by DODGE (U.S. Pat. No. 1 908 696). In the U.S. Pat. Nos. 3 388 972, 3 546 140 and 3 790 505, the American Company C.C.I. discloses the use of ternary compositions Cu-Zn-Al for the conversion at low temperature of carbon monoxide (CO) and for the synthesis of methanol. In the French Pat. No. 2 113 467 the SHELL Company recommends the use of Cu-Zn-Dy catalysts for the synthesis of methanol; Dy or didymium being the mixture of at least two oxides of rare earth metals having atomic numbers from 57 to 71 included. This company shows that the best results are obtained with catalysts containing several oxides of rare earth metals; the use of aluminum is not suggested.

Various methods for preparing Cu-Zn-Al catalysts are disclosed, particularly in the U.S. Pat. No. 3 923 694 (I.C.I.) and U.S. Pat. No. 4 279 781 (United Catalysts).

The addition of precious metals, as chlorides, has been claimed, in particular in the U.S. Pat. No. 4 257 920 which relates to Cu-Al-Zn catalysts prepared by admixing oxides and/or carbonates of said metals in the presence of an aluminous cement, the catalyst further containing at least one oxide of rare earth metals of atomic numbers from 57 to 71 included.

SUMMARY OF THE INVENTION

The present invention concerns a process for manufacturing said catalysts; as a matter of fact, it has been discovered that particularly active, selective and stable catalysts may be obtained by a process comprising the following succession of steps:

Step a: Coprecipitation by an alkaline reactant of a precursor containing copper, aluminum, zinc metals, optionally with silver and/or palladium and/or rhenium, at a pH set at a value from about 6.3 to 7.3, preferably about from 6.6 to 7.0 pH units.

Step b: Washing so as to reduce the alkali metal content (supplied by the coprecipitation reactant) of the washed precipitate to less than about 0.06% by weight, preferentially less than about 0.04% with respect to the metals.

Step c: Coprecipitation with an ammonium compound (hydroxide, carbonate, hydroxycarbonate) of a rare earth and/or zirconium compound or mixture of compounds, for example from the nitrate of the same metal.

Step d: Washing so as to reduce the nitrogen content of the washed precipitate to less than about 3% by weight and preferably less than about 1% with respect to the metals.

Step e: Admixture of both precipitates so as to obtain an intimate dispersion, on the scale of 0.01–0.1$\mu$ (micron) of the rare earth and/or zirconium precipitate and of the precursor containing Cu, Al, Zn metals and optionally Pd and/or Ag and/or Re.

Step f: Drying, followed with a thermal activation.

At least one metal M from the group consisting of palladium, rhenium, platinum and silver may also be optionally deposited by impregnation of the activated catalyst. It has been discovered that the chloride and sulfate ions have a negative effect on their activity and that improved performances are obtained with other salts. For example acetylacetonates, nitrates, amminated complexes will be used; rhenium is preferably used as perrhenic acid or salts thereof.

The catalysts according to the invention contain the above mentioned metals in the following proportions,:
copper: 20–80%, preferentially 45–70%
zinc: 5–50%, preferentially 15–35%
aluminum: 2–30%, preferentially 4–20%
rare earth metals and/or zirconium: 2–20% preferentially 5–18%

They may optionally further contain up to 10% by weight for example and preferentially up to 5% by weight of metals comprising at least one metal M selected from the group formed of palladium, rhenium, platinum and silver.

When the catalysts contain one or more metals from the group consisting of palladium, rhenium and platinum, the content of these metals, expressed by weight, is more preferably from 0.01 to 1% and, when they contain silver, the silver content is more preferably from 0.5 to 5%.

Cu, Zn, Al metals with, separately or simultaneously, rare earths, zirconium, palladium, silver, are used as soluble compounds, preferably soluble in acid medium, although the ammino complexes (soluble in ammoniacal medium) of copper, zinc, palladium, may be optionally added to the coprecipitation alkaline and/or ammoniacal reactant.

Soluble oxides (for example $Re_2O_7$), hydroxides, carbonates, hydroxycarbonates soluble in acid medium (e.g. Cu $CO_3$-Cu$(OH)_2$, $ZnCO_3$, Zn $(OH)_2$) nitrates, oxalates, tartarates, citrates, acetates, acetylacetonates or even anionic combinations such as aluminate or perrhenate, will be used for example. The soluble salts used most frequently are the nitrates.

For manufacturing these catalyst masses, it is essential to prepare them according to such techniques as to obtain a product as homogeneous as possible and to avoid segregation of the different elements during the different unitary manufacturing steps.

One procedure consists of preparing, by at least one coprecipitation, a hydrated precursor containing Cu, Zn, Al metals and optionally Pd and/or Ag. The coprecipitation reaction is conducted by putting together, under hereinafter defined operating conditions, the solution of soluble salts of Cu, Zn, Al metals, optionally Pd and/or Ag and a solution of sodium and/or potassium carbonate and/or hydrogen carbonate and/or hydroxide, so as to obtain a co-precipitate which, after subsequent washing, forms the hydrated hydroxycarbonate precursor.

By hydroxycarbonate it is meant a hydrated compound wherein hydroxyl groups are at least partly substituted with carbonate ions; said carbonate ions may be introduced during the coprecipitation (for example precipitation by carbonates) or may originate from a reaction with dissolved $CO_2$ and/or atmospheric $CO_2$ which may interact with the precipitate during the filtration, washing and drying steps.

All the techniques and apparatuses described in the prior art may be used or applied for carrying out the invention. For example, the solution of salts of Cu, Zn, Al and optionally Pd and/or Ag may be added to the alkaline solution or inversely. Preferably, both solutions will be added simultaneously and their flow rates adjusted in relation with the pH measured in the reaction zone, in a reactor comprising an efficient stirring system. Preferably both solutions are contacted in a zone of maximum turbulence defined by the volume surrounding the stirring apparatus, inside the reaction volume.

The average residence time, expessed in minutes, is defined as the ratio of the total volume flow rate (liters/minute) of the solutions introduced into the reactor to the volume of said reactor, expressed in liters.

In a "batchwise" operated reactor, where the residence time is about from 30 to 300 minutes, preferably about 60 to 180 minutes, the reactants are continuously introduced without corresponding withdrawal of the reaction product, this reaction product remaining in the presence of the continuously fed reactants. This type of reactor, whose volume (in view of the specifications of concentration of the solutions and of the catalyst amounts to prepare) vary from about 1 liter of about 1000 liters or more, is operated at variable concentrations, the other operating conditions remaining constant during the precipitation itself. This reaction mode is well adapted to the preparation of crystallized compounds.

An embodiment of the invention consists of reacting at a temperature of at least about 60° C. and preferably about 70° C., a solution of salts of Cu, Zn, Al metals, optionally Pd and/or Ag, at a maximum total metals concentration of about 2 gram-atoms per liter, e.g. a concentration from 0.3 to 1.8 gram-atoms of metals per liter, with a solution of sodium and/or potassium and/or ammonium carbonate and/or hydrogen carbonate and/or hydroxide at a total maximum concentration of about 4 gram-atoms (e.g. about 0.6–3.6 gram-atoms) of alkali metals per liter, the coprecipitation reaction (step a) being conducted at a pH set at a value ranging from about 6.3 to 7.3, preferably from 6.6 to 7.0 pH units, and the residence time in the reaction medium being at least about 60 minutes.

There is thus obtained a precipitate containing a hydrated mixed hydroxycarbonate, at least partly crystallized in one or more structures. When the alkali cation is sodium, the alkaline solution may optionally contain, in addition, rhenium, at least partly as perrhenate anion ($ReO_4^-$). The carbonate ion originates randomly from any one of the two solutions or may result from the interaction of dissolved $CO_2$ and atmospheric $CO_2$ with the formed precipitate.

The one or more crystallized compounds may optionally be matured for example at about 50°–80° C. under atmospheric pressure for 15 minutes to 5 hours, in the presence of the mother liquors or still of the washing waters. During this maturation operation, the pH is generally increased to a value at most 1.5 pH unit higher than the precipitation pH. Unexpectedly, it is observed that this maturation treatment improves the crystallinity and/or increases the size of the crystallites of the crystallized hydrated precursor.

The maturation operation may be conducted in the same reactor, after discontinuation of the reactants supply. It is also possible, when proceeding by continuous precipitation, to recover the precipitate obtained under steady state conditions (temperature, concentrations, pH, velocity of reactants feed) and to mature it, after optional washing, in another reactor.

Preferably, the reaction temperature for the manufacture of the crystallized precipitate will be at least about 70° C., the concentration of the solution of Cu, Zn, Al, optionally Pd, Ag, Re metals salts will range from about 0.6 to 1.5 g.at of metals per liter and that of the alkali metals compounds from about 1.2 to 3.0 g.at of alkali metals per liter, and the reaction time will be at least about 120 minutes. The solution of alkali metals is preferably a carbonate solution.

After precipitation and optional maturation in the mother liquors, the crystallized precipitate is washed (step b) so as to reduce its alkali content (expressed as alkali weight in proportion to the total metal weight) to less than about 0.06% by weight, said content of residual alkali being generally and preferably lower than 0.04% by weight; then the precipitate is optionally matured in the washing waters.

The compound comprising at least one metal Ln from the group of the rare earths having atomic numbers from 57 to 71 included, and/or zirconium is prepared by coprecipitation reaction (step c) in the above-mentioned operating conditions, from at least one of the above-mentioned soluble compounds, the co-precipitating agent being at least one ammonium cation compound (hydroxide, carbonate, hydrogen carbonate). Only the co-precipitation pH may vary within a broader range than that above-mentioned; a coprecipitation pH from about 6 to 8 pH units gives satisfactory results.

Similarly, after coprecipitation, the hydrated compound containing at least one Ln and/or zirconium metal may optionally be matured in the above-described operating conditions.

After precipitation and optional maturation in the mother liquors, the precipitate containing at least one Ln metal and/or zirconium is washed (step d) so as to reduce its nitrogen content ($NH_4^+$ and optionally $NO_3^-$) to a value of less than 3% of the total metals weight, preferentially less than 1% by weight.

The two washed coprecipitates obtained as above-mentioned are the admixed (step e) in an apparatus adapted to achieve as homogeneous a dispersion as possible, of the two products into each other. The dispersion may be measured with a microsonde of Castaing or still by X microanalysis with a scanning micoscope (STEM). The best results are obtained with a substantially homogeneous dispersion on a scale of 0.01–0.1$\mu$ (micron).

The substantially homogeneous dispersion of the two resultant coprecipitates is obtained by taking advantage of their thixotropic properties, by subjecting the mixture to sufficiently high shear forces, applied to the product through revolving blades, discs, cylinders or by passage through orifices, for example through the Werner, Cowles, Waring, Hockmeyer, Rousselle mixers or through certain roller mixers. After the shearing mixing has been discontinued, decantation and/or segregation must not be observed.

Drying of the mixed homogenized product may be achieved by any known process; for example by spray-drying. A substantially homogeneous product is obtained, as calibrated powder containing about 60–80% by weight of oxides equivalent. The product may also be dried in an oven, for example at about 50°–150° C., under air scavenging, so as to reduce, if necessary, its potential oxides content to about 60–80% by weight. It is recommended to avoid the stagnation of the precipitate in the presence of steam partial pressures close to the saturation vapor pressure at the considered drying temperature. Such treatments may result in a partial dehydration of the precipitate with a crystallization of cupric oxide to big crystallites.

The thermal activation consists of treating the dried precipitate at a temperature of about 250°–500° C., preferably about 300°–380° C., for a sufficient time, e.g. at least 0.5 hour, to obtain a substantially homogeneous activated catalyst containing no more than 12% by weight of volatile matters (the proportion of volatile matters is measured for example by activating, in the presence of air, a given weight of product, placed in a boat and roasted at 500°–600° C. for 4 hours).

The thermal activation may be conducted for example in the presence of an inert gas of 0–50% oxygen content.

The drying and thermal activation (step f) may also be combined by using the techniques of flash-roasting or spray-calcination, the product being then pulverized in a stream of combustion gas.

The catalyst, thermally activated at a temperature of about 250°–500° C. and optionally crushed may then optionally be contacted with an aqueous or organic solution of at least one metal M, selected from the group consisting of palladium, platinum, rhenium and/or silver, so as to substantially uniformly disperse said metal and to obtain, after drying and thermal activation as above stated, a catalyst wherein said metal is well dispersed (the dispersion may be measured for example by chemisorption of the reacting gases CO, $H_2$, on said metal). With the exception of halides and sulfates, all of the soluble salts, e.g. nitrates, acetylacetonates, as well as complexes, for example nitrosamminated, amminated or carbonylated complexes, can be used.

The shaping of the catalyst may be achieved by any known process, for example by treatment of the wet precipitate after deposition of additional metals, of the dried precipitate, of the thermally activated precipitate; for the shaping operation, extrusion, bowl granulation, oil-drop, can be used. The thermally activated homogeneous product may optionally be crushed, for example to particles of less than 0.5 mm, admixed in a proportion of 0.5–5% of its weight with a pelletizing adjuvant selected from the group consisting of graphite, stearic acid, stearates and, optionally, a porosity adjuvant selected from cellulose and cellulose containing powders of vegetable origin, ammonium carbonates, combustible textile fibers and naphthalene. Finally, the product may be pelletized to solid cylinders of 3–6 mm diameter or toric cylinders of 3–6 mm external diameter and 1–4 mm internal diameter and of 2–6 mm height.

The catalyst shaped to pellets will be optionally subjected to a final thermal activation in the above-mentioned operating conditions.

The thermally activated catalyst essentially consists of a substantially homogeneous association of oxides. In this homogeneous association of oxides, the metals, particularly copper, zinc, aluminum and other additional metal elements are distributed homogeneously, at a scale of 0.01–0.1 $\mu$m. The specific surface of said catalysts varies from about 50 to about 150 $m^2 g^{-1}$.

The conditions of use of said catalyst for manufacturing methanol are usually as follows: the catalyst charge, in the reactor, is first prereduced by a mixture of inert gas (e.g. nitrogen) with at least one reducing compound selected from the group consisting of hydrogen, carbon monoxide, alcohols, $C_1$ and $C_2$ aldehydes, the molar ratio "reducing compound/reducing compound+inert gas" being from 0.001:1 to 1:1.

The reduction temperature generally varies from about 100° to 300° C. but preferably from about 140° to 260° C., the total pressure is usually about 0.1–10 MPa and preferably about 0.1–6 MPa; The hourly volume velocity is usually from about $10^2$ to $4.10^4$ $hour^{-1}$ and preferably from about $5.10^2$ to $10^4$ $hour^{-1}$ (under normal temperature and pressure (NTP).

The reduction is first conducted, for example, at about 140°–160° C. in the presence of the above-mentioned reducing mixture and with a molar ratio "reducing gas/reducing gas+inert gas" ranging from about 0.001 to 0.1 preferentially from about 0.005 to 0.05, for a sufficient time to obtain the same concentrations of reducing gas at the inlet and at the outlet of the reactor (thus making obvious that the first reduction step is completed). It may also be advantageous, in a second step, to increase the temperature and, optionally, the concentration of reducing gas, and to continue the reduction under more severe thermal conditions.

The reduction temperature then varies between about 160° and about 240° C., the molar ratio "reducing gas/reducing gas+inert gas" is then about 0.01–1, and preferentially 0.05–1, the pressure and hourly volume velocity remaining within the above-mentioned ranges.

The prereduction of the catalyst will be preferentially conducted in liquid phase when, subsequently, the methanol synthesis reaction is performed in liquid phase.

The methanol synthesis reaction itself is conducted in the following operating conditions: the pressure is usually about 2–15 MPa, preferably about 4–15 MPa, the molar ratio "$H_2/2$ CO+3 $CO_2$" is advantageously about 0.4–10 but preferably 0.5–4, when the reaction is conducted in gaseous phase, and preferably about 0.5–1.5 when the reaction is conducted in liquid phase. The temperature ranges from about 200° to 300° C., preferably from about 220° to 270° C.

The hourly volume velocity (expressed in volume NTP of gas mixture per volume of catalyst and per hour) is usually from about 1,500 to 60,000 $h^{-1}$ and preferably from 2,000 to 20,000 $h^{-1}$.

The catalyst may be used as fine calibrated powder (about 10–700 $\mu$m) or as particles of about 2–10 mm diameter, in the presence of a gas phase or of a liquid (in the operating conditions) phase and a gas phase. The liquid phase may consist of one or more hydrocarbons having at least 5 and preferably at least 10 carbon atoms.

In this embodiment, it is preferable that the superficial velocities of the gas and liquid, under the temperature and pressure conditions of the process, be at least about 1.5 cm/sec. and preferably at least about 3 cm/sec. By superficial velocity, it is intended to mean the ratio of the flow rate by volume to the cross-sectional area of the reactor, when empty of catalyst.

The conditions of use of said catalysts for decomposing $C_1$ to $C_5$ primary alcohols and particularly methanol are usually as follows: the catalyst charge, in the reactor, is first prereduced by a mixture of inert gas (e.g. nitrogen) and at least one reducing compound selected from the group consisting of hydrogen, carbon monoxide, $C_1$ and $C_2$ alcohols and aldehydes, the molar ratio: "reducing compound/reducing compound+inert gas" being from 0.001:1 to 1:1.

The reduction temperature ranges from about 100° to 300° C. but preferably from about 140° to 260° C.; the total pressure is usually from about 0.1 to 10 MPa and preferably from about 0.1 to 6 MPa; the hourly volume velocity is usually from about $10^2$ to $4.10^4$ hour$^{-1}$ and preferably from about $5.10^2$ to $10^4$ hour$^{-1}$ (Normal Temperature and Pressure (NTP).

The reduction is first conducted, for example at about 140°–160° C., in the presence of the above-mentioned reducing mixture and with a molar ratio "reducing gas/reducing gas+inert gas" ranging from about 0.001 to 0.1 and preferentially from about 0.005 to 0.05, for a sufficient time to obtain the same concentrations of reducing gas at the inlet and the outlet of the reactor (thus making obvious that the first reducing step is completed). It may be advantageous in a second step to increase the temperature and optionally the concentration of reducing gas and to continue the reduction under more severe thermal conditions.

The reduction temperature varies from about 160° to about 240° C. The molar ratio "reducing gas/reducing gas+inert gas" is then from about 0.01 to 1, preferentially from about 0.05 to 1, the pressure and hourly volume velocity being within the above-mentioned ranges.

The decomposition reaction itself is conducted under the following operating conditions: the pressure is usually about 1–10 MPa, preferably about 2–5 MPa. The temperature is about 200°–400° C., preferably about 220°–320° C.

The hourly volume velocity of the charge (expressed in liters of charge per liter of catalyst and per hour) is usually about 0.1–5 h$^{-1}$ and preferably about 0.5–3 h$^{-1}$.

EXAMPLES

The following examples describe various embodiments of the invention without limiting the scope thereof.

EXAMPLES 1 TO 18

First of all the manufacture of catalysts A to H, whose characteristics are reported in Table II, is described. The manufacturing conditions are summarized in Table III.

The manufacture of catalysts A to C and F to H are described more in detail hereinafter and summarized in Table III for the other catalysts. The manufacture of catalysts A, $A_1$, $A_2$, D, E, $E_1$, F, G, $K_1$ is described by way of comparison.

CATALYSTS A: (comparison)

241.6 g. of trihydrated cupric nitrate (1 g.at Cu), 150 g of nonahydrated aluminum nitrate (0.4 g.at Al), 89.25 g. of hexahydrated zinc nitrate (0.3 g.at Zn) are dissolved into 1.5 liters of water. The solution (solution A, 1.133 g.at of metals/liter) is heated to 80° C.

Separately, 234.25 g. of disodic carbonate are dissolved into 1.5 liters of water. The resultant solution B (2.95 g.at Na/l) is heated to 80° C.

Both solutions A and B are simultaneously introduced in 2 hours into a heated reactor of 10 liters capacity, containing 3 liters of water at a temperature of 80° C. The flow rates are adjusted in relation with the pH which varies from 6.75 to 6.95. The obtained precipitate is matured at 80° C. in its mother liquors for 30 minutes before being washed three times with 10 liters of water. This crystallized, wet precipitate contains about 22% by weight of non-alkali metal oxides and 132 ppm by weight of sodium with respect to the oxides. It is dried in a ventilated oven at 40° C. for 16 hours, then at 90° C. for 4 hours (it then contains 72% by weight of oxides), then activated for 4 hours at 350° C. in air. Its content of residual volatile matters is then 5%. The powder obtained by crushing to a particle size of less than 0.5 mm is admixed with 2% by weight of graphite, pelletized to cylinders of 4 mm diameter and 3.5 mm length, then activated for 3 hours at 350° C. in air. About 130 g. of catalyst having a specific surface of 65 m$^2$/g. are thus obtained.

CATALYST $A_1$: (comparison)

The manufacture of catalyst $A_1$ is performed according to the method described for catalyst A, except that solution A contains, in addition, 43.30 g. of hexahydrated lanthanum nitrate (0.1 g.at. La) i.e. a total of 1.2 g.at. of metals per liter. Solution B is obtained by dissolving 238.5 g. of sodium carbonate into 1.5 l of water (3 g.at. Na/l).

CATALYST $A_2$: (comparison)

The manufacture of catalyst $A_2$ is identical to that described for catalyst $A_1$ except that the amount of washing water is considerably increased so as to lower the sodium content of the final catalyst to 600 ppm by weight.

CATALYST B:

241.6 g. of trihydrated cupric nitrate (1 g.at. Cu), 56.25 g of nonahydrated aluminum nitrate (0.15 g.at. Al), 89.25 g of hexahydrated zinc nitrate (0.3 g.at. Zn), are dissolved into 1.5 liters of water. The solution (solution A, 0.966 g.at. of metals/liter) is heated to 80° C.

Separately, 199 g of sodium carbonate are dissolved into 1.5 liters of water. This solution B (2.50 g.at. Na/l) is heated to 80° C.

In a heated reactor of 10 liters capacity, containing 3 liters of water heated to 80° C., both solutions A and B are simultaneously added in 2 hours. The flow rates are adjusted in relation with the pH, the latter varying from 6.75 to 6.85. The obtained precipitate (P) is matured at 80° C. in the mother liquors for 30 minutes. It is then washed 3 times with 10 liters of water. Its sodium content is 180 ppm by weight. Table I gives the Miller indexes of the rhombohedral phase of hydroxycarbonate type of the obtained crystallized precipitate.

In a second reactor of 10 liters capacity, containing 3 liters of water heated to 80° C., both solutions C and D are simultaneously added.

The first solution (C) contains 65.15 g of hexahydrated cerium nitrate dissolved in 1 liter of water (0.15 g.at/l); it is heated to 80° C.

The second solution (D) is a 0.5 molar ammonia solution.

The feed rate of each solution is adjusted in relation with the pH which is maintained at about 7, the precipitation temperature being set at 80° C. The obtained cerium hydroxide precipitate is washed three times with 10 liters of water. Its nitrogen content is then lower than 1% by weight with respect to the potential oxide weight.

In a reactor of 10 liters capacity containing 6 liters of water at 20° C., the above-obtained precipitate (P) and cerium hydroxide are admixed. An efficient stirring of this suspension by a turbine provides for an intimate dispersion, at a scale of 0.01–0.1 micron, of all the constituents of this new precursor. The drying, roasting and shaping steps are identical to those described for catalyst A.

CATALYST C

The methods for manufacturing precipitate P (mixture containing copper, aluminum and zinc hydroxycarbonates) and a rare earths hydroxide, are identical to those used for the manufacture of catalyst B. Only the mixing method is different. As a matter of fact, the two wet precipitates, separated from their last washing water, are admixed in wet state into a mixer. After a mixing time of about ½ hour whereby a good dispersion of all the elements is achieved (at a scale of 0.1 micron) the resultant product is subjected, as in the above examples, to the same drying, activation and shaping steps.

CATALYST D: (comparison)

The dry product (containing Cu, Al and Zn hydroxycarbonates), obtained according to the preparation of catalyst A, is mechanically admixed in dry state with a rare earth carbonate ($La_2(CO_3)_3$, $sH_2O$). The resultant powder, homogeneous (at the micron scale), is then activated in air at 350° C. for 4 hours and then shaped by the same method as for catalyst A.

CATALYST E: (comparison)

The product activated in air at 350° C., obtained according to the preparation method of catalyst A (Cu, Zn and Al mixed oxide) is mechanically admixed in dry state with a rare earth oxide ($La_2O_3$). After homogenization at the micron scale of the different oxides, the powder is shaped and then reactivated in air at 350° C.

CATALYST $E_1$: (comparison)

Catalyst $E_1$ is prepared in the same manner as catalyst A, except that the thermally activated and shaped copper, aluminum, zinc precursor is subjected to a dry impregnation with a lanthanum nitrate solution, followed with a drying and a thermal activation.

According to the method described for manufacturing catalyst A, a solution containing 1 gram-atom of copper, 0.35 gram-atom of aluminum and 0.3 gram-atom of zinc is coprecipitated as hydroxycarbonate with a solution of sodium carbonate containing 2.90 gram-atoms of sodium per liter. The resultant coprecipitate is then washed, dried and roasted as described for catalyst A.

The resultant product is finally shaped by pelletizing as described for catalyst A.

The obtained pellets are impregnated in dry condition with a volume of lanthanum nitrate solution (0.05 mole) corresponding to the pore volume of the catalyst (35 cc). Then the solvent is evaporated by rotating the pellets under hot air scavenging, then drying for 2 hours at 100° C., 2 further hours at 120° C., the product being then activated for 2 hours at 350° C. in air.

CATALYST F: (comparison)

The manufacture of catalyst F is identical to that of catalyst A except that a certain amount of sodium perrhenate is added to the sodium carbonate solution. Solution A is formed by dissolving 241.6 g of trihydrated copper nitrate (1 g.at. Cu), 150 g of nonahydrated aluminum nitrate (0.4 g.at Al) and 148.75 g of hexahydrated zinc nitrate (0.5 g.at Zn) into 1.5 liters of water. Solution A, containing 1.27 g.at. of metals/liter is heated to 80° C. Solution B is formed by dissolving 261.8 g of sodium carbonate (3.29 g.at./liter Na) and 2.73 g of sodium perrhenate (Na Re $O_4$) (0.01 g.at. Re) into 1.5 liters of water. Solution B is then heated to 80° C.

CATALYST $F_1$

The preparation of catalyst $F_1$ is identical to that of Catalyst B, except that:

Solution A is formed by dissolving into 1.5 liters of water 241.6 g of trihydrated copper nitrate (1 g.at. Cu), 112.5 g of nonahydrated aluminum nitrate (0.3 g.at. Al) and 119 g of hexahydrated zinc nitrate (0.4 g.at. Zn). Solution A (1.133 g.at. of metals/liter) is heated to 80° C.

Solution B is formed by dissolving into 1.5 liters of water 234.2 g of sodium carbonate and 2.7 g of sodium perrhenate (Na Re $O_4$) (0.01 g.at. Re).

The crystallized precipitate $P_1$, obtained according to the above described procedure for manufacturing catalyst B, is washed 3 times with 12 liters of water and then dried on filter.

In a second reactor, lanthanum hydroxide is precipitated at 80° C. and at a pH of 7, from a solution obtained by dissolving 43.3 g of lanthanum nitrate into 0.5 l of water (0.1 g.at La) and a 0.1 molar ammonia solution. The resultant precipitate is washed 3 times with 5 liters of water and then dried over filter. Precipitate $P_1$ is admixed with the lanthanum hydroxide precipitate by wet mixing for 30 minutes. The obtained homogeneous product is then dried for 6 hours at 90° C., then 12 hours at 120° C. It is then activated in air at 350° C. for 4 hours and shaped by pelletizing.

CATALYST G: (comparison)

Catalyst G is prepared in the same manner as catalyst A, except that silver nitrate is added to the solution of copper, aluminum and zinc nitrates.

Solution A is formed by dissolving 241.6 g of trihydrated copper nitrate (1 g.at Cu), 112.5 g of nonahydrated aluminum nitrate (0.3 g.at Al), 119 g of hexahydrated zinc nitrate (0.4 g.at Zn), 6.8 g of silver nitrate (0.04 g.at Ag) into 1.5 liters of water. Solution A, containing 1.16 g.at of metals/liter, is heated to 80° C.

Solution B is formed by dissolving 240 g of sodium carbonate (3.02 g.at/liter) into 1.5 liters of water.

CATALYST G2

The manufacturing procedure is identical to that of catalyst B, except that silver nitrate is added to the solution of copper, aluminum and zinc nitrates.

Solution A is formed by dissolving 241.6 g of trihydrated copper nitrate (1 g.at Cu), 112.5 g of nonahydrated aluminum nitrate (0.3 g.at Al), 119 g of hexahydrated zinc nitrate (0.4 g.at Zn), 6.8 g of silver nitrate (0.04 g.at Ag) into 2.5 liters of water. Solution A, containing 0.7 g.at of metals/liter, is heated to 80° C.

Solution B is formed by dissolving 240 g of sodium carbonate (3.02 g. at Na), into 1.5 liters of water; it is heated to 80° C.

In a second reactor, 0.5 liter of a solution C containing 0.05 mole of praseodymium nitrate and a 0.1M ammonia solution are simultaneously added.

The two resultant precipitates, perfectly washed, are then admixed by stirring in suspension in a strongly stirred reactor. After water removal, drying and activation in air, the catalyst is shaped by pelletizing.

CATALYST H

The manufacturing procedure is identical to that of catalyst B, except that dihydrated zirconyl nitrate is added to the solution of cerium nitrate. Precipate $P_1$ is formed from a solution containing 241.6 g of trihydrated copper nitrate (1 g.at Cu), 75 g of nonahydrated aluminum nitrate (0.2 g.at Al), 89.25 g of hexahydrated zinc nitrate (0.3 g.at Zn) and a solution containing 207 g of sodium carbonate. The precipitation takes place in a reactor at a temperature of 80° C. by simultaneous addition of both solutions at a pH adjusted to 6.8.

The precipitate of rare earths hydroxide is formed by simultaneous addition, in a reactor, of a solution containing 43.43 g of hexahydrated cerium nitrate (0.1 g.at Ce) and 26.7 g of dihydrated zirconyl nitrate (0.1 g.at Zr) and of a 0.5 molar ammonia solution. The pH is maintained constant at a value of 7 and the temperature is 80° C.

Both precipitates, after washings, are admixed in suspension and by strong stirring form an intimate dispersion at a scale of 0.01–0.1 micron, before drying, activation in air and shaping.

CATALYST H₁

The manufacture of catalyst $H_1$ is identical to that of catalyst B, except that another metal is added by impregnation of the precursor, activated in air and shaped. Precipitate $P_2$ is obtained from a solution containing 241.6 g of trihydrated copper nitrate (1 g.at Cu), 56.25 g of nonahydrated aluminum nitrate (0.15 g.at Al), 89.25 g of hexahydrated zinc nitrate (0.3 g.at Zn) and a solution containing 215 g of sodium carbonate.

The co-precipitate of a rare earth metal and a zirconium compound is obtained from a solution containing 43.8 g of hexahydrated neodymium nitrate (0.1 g.at Nd) and 42.95 g of pentahydrated zirconium nitrate (0.1 g.at Zr) and a 0.5 molar ammonia solution.

After washing of each precipitate, admixture in suspension, activation in air and pelletizing, the pellets are impregnated with a solution containing 1.55 g of palladium bis acetylacetonate (0.005 g.at Pd) in 40 cc of toluene. The pellets are then dried at 90° C. in a ventilated stove and then activated in air at 350° C.

TESTS OF THE CATALYSTS IN GASEOUS PHASE

All the catalysts are tested in a pilot unit operating continuously and with 20 ml of catalyst. The catalysts were preliminarily prereduced in the following conditions:
6% hydrogen in nitrogen
atmospheric pressure
space velocity of the gas mixture of 3000 h$^{-1}$
reduction stages:
8 h at 160° C.
3 h at 190° C.
3 h at 210° C.
3 h at 240° C.

The development of each test is as follows:
(a) Pressurization of the pilot unit at 6 MPa with nitrogen.
(b) Introduction of the CO+CO₂+H₂ mixture under 6 MPa (megapascals) at 200° C.
(c) Operating conditions:

| | |
|---|---|
| average temperature of the catalyst bed: | 230° C. |
| total pressure | P = 6 MPa |
| VVH = 10,000 h$^{-1}$ | |
| VVH = (H₂ + CO + CO₂) flow rate in liters | |
| (NTP)/hour/catalyst liter | |
| Composition of synthesis gas $\dfrac{H_2}{2\,CO + 3\,CO_2}$ = 1.2 | |

The tests results are given in Table IV. The performances are defined as follows:

Productivity by weight to methanol: expressed by the number of methanol grams obtained per hour per gram of catalyst charge.

Selectivity to methanol: ratio of the number of formed methanol moles to the number of (CO+CO₂) moles which disappeared.

The selectivity C is expressed by:

$$C = 100 \times \frac{\text{Number of formed methanol moles}}{(CO + CO_2) \text{ moles at inlet} - (CO + CO_2) \text{ moles at the outlet}}$$

EXAMPLE 19

The reactor has a 4 cm diameter, a 3 meters useful height and it contains 1 liter of catalyst ($F_1$).

The catalyst reduction is performed in gaseous phase under atmospheric pressure at 200°–260° C. by simultaneous injection into the reactor of 3 m³/h of nitrogen and 200 cc/h of methanol.

After reduction, the reactor is fed with a $C_{12}$–$C_{18}$ paraffinic cut at a rate of 270 l/h (superficial velocity at the selected conditions: 7.5 cm/s) and with a synthesis gas under a pressure of 7.5 MPa. The operating conditions are:

| | |
|---|---|
| total pressure | P = 75 MPa |
| temperature | t = 250° C. |
| hourly volume velocity of the gas | VVH$_g$ = 15,800 h$^{-1}$ |
| synthesis gas composition $\dfrac{H_2}{2\,CO + 3\,CO_2}$ = 1 | |
| hourly volume liquid velocity | VVH$_l$ = 270 h$^{-1}$ |

The productivity by weight P of catalyst to methanol is quickly stabilized at 0.5 g of methanol per catalyst gram per hour.

EXAMPLE 20

150 cc of a $C_{12}$–$C_{18}$ paraffinic cut and 10 g of finely crushed (50–100μ) catalyst B are introduced in a strongly stirred reactor of the Grignard type, of 0.5 liter volume.

The catalyst reduction is conducted in situ, in liquid phase, with pure hydrogen at 240° C., under a pressure of 7.5 MPa. After reduction, hydrogen is replaced with a $H_2+CO+CO_2$ mixture having such a composition that $$\frac{H_2}{2\,CO + 3\,CO_2} = 1.4$$

At 250° C., under a pressure of 7.5 MPa, the productivity is 0.6-0.7 gram of methanol per gram of catalyst per hour.

EXAMPLE 21

A $C_{12}$–$C_{18}$ paraffinic cut wherein is suspended a finely crushed (50-200μ) catalyst (H) in a proportion of 0.2 kg/liter and containing synthesis gas is circulated through a tubular reactor of 0.05 m diameter and 2 m height. Methanol has been produced at a rate of 1.2 kg per kilogram of catalyst per hour, under the following operation conditions:

| | |
|---|---|
| temperature | T = 240° C. |
| total pressure | P = 7.5 MPa |
| linear velocity of the suspension | 0.2 cm/s |
| hourly volume velocity of gas/ catalyst volume in the reactor | $VVH_{gas} = 10{,}000\ h^{-1}$ | composition of the synthesis gas $\dfrac{H_2}{2\,CO + 3\,CO_2} = 1$

EXAMPLE 22

10 g of catalyst (C) are reduced for a few hours under atmospheric pressure with 5% hydrogen contained in nitrogen, in a tubular reactor at 140°-260° C. After reduction, methanol is decomposed. At a temperature of 290° C., at a pressure of 3.0 MPa and a liquid phase velocity of 3 $h^{-1}$, more than 95% of the methanol are converted.

TABLE I

RHOMBOHEDRAL PHASE OF HYDROXYCARBONATE TYPE HEXAGONAL MESH a = 0.305 nm C = 2.24 nm SPACE GROUP R - 3M

| MILLER INDEX | d (nm) | i/Lu |
|---|---|---|
| 003 | 0.7557 | 100 |
| 006 | 0.3757 | 75 |
| 101 | 0.2630 | 15 |
| 012 | 0.2585 | 60 |
| 104 | 0.2402 | 10 |
| 015 | 0.2292 | 40 |
| 107 | 0.2053 | 5 |
| 018 | 0.1930 | 30 |
| 1010 | 0.1719 | 15 |
| 0111 | 0.1625 | 10 |
| 110 | 0.1535 | 15 |
| 113 | 0.1507 | 15 |
| 1013 | 0.1454 | 10 |
| 116 | 0.1428 | 10 |
| 0114 | 0.1362 | 5 |

Recording conditions: Cu $K_\alpha$ 35 KV mA
Rear monochromator (graphite)

TABLE II
CATALYSTS COMPOSITION

| CATALYSTS (formulas) | ATOMIC RATIO | | | | | Metal % b.w. in proportion to ϵ metals weight | | | | | | CONTENT (ppm) | |
|---|---|---|---|---|---|---|---|---|---|---|---|---|---|
| | Cu/Al | Cu/Zn | Cu/M | Cu/Ln | Cu/Zr | Cu | Al | Zn | Ln | M | Zr | Na | $N_2$ |
| A   $Cu_1Al_{0.4}Zn_{0.3}$ | 2.5 | 3.33 | | | | 67.63 | 11.50 | 20.86 | | | | 132 | — |
| $A_1$ $Cu_1Al_{0.3}Zn_{0.3}La_{0.1}$ | 3.33 | 3.33 | | 10 | | 60.43 | 7.71 | 18.65 | 13.22 | | | 1500 | 50 |
| $A_2$ $Cu_1Al_{0.35}Zn_{0.4}La_{0.05}$ | 2.86 | 2.5 | | 20 | | 59.95 | 8.91 | 24.67 | 6.55 | | | 600 | 50 |
| B   $Cu_1Al_{0.15}Zn_{0.3} + Ce_{0.15}$ | 6.66 | 3.33 | | 6.66 | | 58.69 | 3.74 | 18.12 | 19.47 | | | 180 | 550 |
| C   $Cu_1Al_{0.2}Zn_{0.4} + Nd_{0.1}$ | 5 | 2.5 | | 10 | | 58.02 | 4.93 | 23.86 | 13.17 | | | 190 | 650 |
| D   $Cu_1Al_{0.3}Zn_{0.5} + La_{0.1}$ | 3.33 | 2 | | 10 | | 53.75 | 6.86 | 27.64 | 11.76 | | | 100 | — |
| E   $Cu_1Al_{0.25}Zn_{0.4} + La_{0.05}$ | 4 | 2.5 | | 20 | | 61.47 | 6.53 | 25.29 | 6.72 | | | 120 | — |
| $E_1$ $Cu_1Al_{0.35}Zn_{0.3} + La_{0.05}$ | 2.86 | 3.33 | | 20 | | 63.84 | 9.49 | 19.70 | 6.98 | | | 140 | — |
| F   $Cu_1Al_{0.4}Zn_{0.5}Re_{0.01}$ | 2.5 | 2 | 100 | | | 58.36 | 9.93 | 30.00 | | 1.71 | | 70 | — |
| $F_1$ $Cu_1Al_{0.3}Zn_{0.4}Re_{0.01} + La_{0.1}$ | 3.33 | 2.5 | 100 | 10 | | 55.96 | 7.14 | 23.02 | 12.24 | 1.64 | | 140 | 700 |
| G   $Cu_1Al_{0.3}Zn_{0.4}Ag_{0.04}$ | 3.33 | 2.5 | 25 | | | 62.23 | 7.94 | 25.60 | | 4.23 | | 130 | 50 |
| $G_1$ $Cu_1Al_{0.25}Zn_{0.5}Pd_{0.005} + Pr_{0.10}$ | 4 | 2 | 200 | 10 | | 54.07 | 5.68 | 27.80 | 12.0 | 0.47 | | 90 | 600 |
| $G_2$ $Cu_1Al_{0.3}Zn_{0.4}Ag_{0.04} + Pr_{0.05}$ | 3.33 | 2.5 | 25 | 20 | | 58.22 | 7.42 | 23.95 | 6.43 | 3.96 | | 120 | 250 |
| H   $Cu_1Al_{0.2}Zn_{0.3} + Ce_{0.1}Zr_{0.1}$ | 5 | 3.33 | | 10 | 10 | 56.89 | 4.84 | 17.55 | 12.55 | | 8.17 | 120 | 1050 |
| $H_1$ $Cu_1Al_{0.15}Zn_{0.3} + Zr_{0.1}Nd_{0.1}Pd_{0.005}$ | 6.66 | 3.33 | 200 | 10 | 10 | 57.10 | 3.64 | 17.62 | 12.96 | 0.47 | 8.20 | 190 | 650 |
| $H_2$ $Cu_1Al_{0.3}Zn_{0.5}Pd_{0.003} + La_{0.05}Zr_{0.05}$ | 3.33 | 2 | 333 | 20 | 20 | 54.71 | 6.97 | 28.14 | 5.98 | 0.27 | 3.93 | 100 | 400 |
| $K_1$ $Cu_1Al_{0.4}Zn_{0.5} + Pd_{0.005}Pr_{0.1}$ | 2.5 | 2 | 200 | 10 | | 52.23 | 8.88 | 26.86 | 11.59 | 0.44 | | 50 | — |
| $K_2$ $Cu_1Al_{0.3}Zn_{0.5} + La_{0.1}Pt_{0.002}$ | 3.33 | 2 | 500 | 10 | | 53.58 | 6.82 | 27.56 | 11.71 | 0.33 | | 110 | 800 |

TABLE III
CATALYSTS MANUFACTURING PROCEDURE

| CATALYSTS | PRECIPITATE A | | PRECIPITATE B | MIXTURE OF A AND B | | | ADDITION OF OTHER METALS | | |
|---|---|---|---|---|---|---|---|---|---|
| | NITRATES | DISODIC CARBONATE Na SALT | (by $NH_4OH$ 0.5 M) or 0.1 M | SUSPENSION | WET MIXING | DRY MIXING | CARBONATE BEFORE ACTIVATION | OXIDE AFTER ACTIVATION | IMPREGNATION AFTER SHAPING |
| A | $Cu_1Al_{0.4}Zn_{0.3}$ | | | | | | | | |
| $A_1$ | $Cu_1Al_{0.3}Zn_{0.3}La_{0.1}$ | | | | | | | | |
| $A_2$ | $Cu_1Al_{0.35}Zn_{0.4}La_{0.05}$ | | | | | | | | |
| B | $Cu_1Al_{0.15}Zn_{0.3}$ | | $Ce_{0.15}$ | + | | | | | |
| C | $Cu_1Al_{0.2}Zn_{0.4}$ | | $Nd_{0.1}$ | | + | | | | |
| D | $Cu_1Al_{0.3}Zn_{0.5}$ | | | | | | $La_{0.1}$ | | |
| E | $Cu_1Al_{0.25}Zn_{0.4}$ | | | | | | | $La_{0.05}$ | |

TABLE III-continued

| | | CATALYSTS MANUFACTURING PROCEDURE | | | | | | | |
|---|---|---|---|---|---|---|---|---|---|
| | PRECIPITATE A | | PRECIPITATE B | MIXTURE OF A AND B | | | ADDITION OF OTHER METALS | | |
| CATALYSTS | NITRATES | DISODIC CARBONATE Na SALT | (by NH$_4$OH 0.5 M) or 0.1 M | SUSPENSION | WET MIXING | DRY MIXING | CARBONATE BEFORE ACTIVATION | OXIDE AFTER ACTIVATION | IMPREGNATION AFTER SHAPING |
| E$_1$ | Cu$_1$Al$_{0.35}$Zn$_{0.3}$ | | | | | | | | La$_{0.05}$ |
| F | Cu$_1$Al$_{0.4}$Zn$_{0.5}$ | 0.01 ReO$_4^-$ | | | | | | | |
| F$_1$ | Cu$_1$Al$_{0.3}$Zn$_{0.4}$ | 0.01 ReO$_4^-$ | La$_{0.1}$ | | + | | | | |
| G | Cu$_1$Al$_{0.3}$Zn$_{0.4}$Ag$_{0.04}$ | | | | | | | | |
| G$_1$ | Cu$_1$Al$_{0.25}$Zn$_{0.5}$Pd$_{0.005}$ | | Pr$_{0.1}$ | | | + | | | |
| G$_2$ | Cu$_1$Al$_{0.3}$Zn$_{0.4}$Ag$_{0.04}$ | | Pr$_{0.05}$ | + | | | | | |
| H | Cu$_1$Al$_{0.2}$Zn$_{0.3}$ | | Ce$_{0.1}$Zr$_{0.1}$ | + | | | | | |
| H$_1$ | Cu$_1$Al$_{0.15}$Zn$_{0.3}$ | | Nd$_{0.1}$Zr$_{0.1}$ | | + | | | | 0.005 Pd(Acac) |
| H$_2$ | Cu$_1$Al$_{0.3}$Zn$_{0.5}$Pd$_{0.003}$ | | La$_{0.05}$Zr$_{0.05}$ | + | | | | | |
| K$_1$ | Cu$_1$Al$_{0.4}$Zn$_{0.5}$ | | Pr$_{0.1}$ | + | | | | | 0.005 Pd(Cl) |
| K$_2$ | Cu$_1$Al$_{0.3}$Zn$_{0.5}$ | | La$_{0.1}$ | + | | | | | 0.002 Pt(Acac) |

TABLE IV

CATALYSTS PRODUCTIVITY AND SELECTIVITY

| Example of utilisation | CATALYSTS | TEMPERATURE | PRODUCTIVITY (CH$_3$OH g/cata g/h) 100 h | 1000 h | SELECTIVITY "C" to CH$_3$OH |
|---|---|---|---|---|---|
| 1 | A | 230° C. | 0.50 | 0.48 | 99.1 |
| 2 | A$_1$ | " | 0.30 | 0.20 | 99.3 |
| 3 | A$_2$ | " | 0.55 | 0.45 | 99.4 |
| 4 | B | " | 0.60 | 0.58 | 99.5 |
| 5 | C | " | 0.62 | 0.60 | 99.4 |
| 6 | D | " | 0.50 | 0.46 | 99.4 |
| 7 | E | " | 0.53 | 0.50 | 99.2 |
| 8 | E$_1$ | " | 0.44 | 0.39 | 98.8 |
| 9 | F | " | 0.55 | 0.51 | 99.0 |
| 10 | F$_1$ | " | 0.62 | 0.60 | 99.6 |
| 11 | G | " | 0.56 | 0.50 | 99.1 |
| 12 | G$_1$ | " | 0.60 | 0.57 | 99.6 |
| 13 | G$_2$ | " | 0.63 | 0.61 | 99.4 |
| 14 | H | " | 0.65 | 0.64 | 99.5 |
| 15 | H$_1$ | " | 0.62 | 0.57 | 99.5 |
| 16 | H$_2$ | " | 0.70 | 0.69 | 99.7 |
| 17 | K$_1$ | " | 0.44 | 0.34 | 98.6 |
| 18 | K$_2$ | " | 0.67 | 0.63 | 99.0 |

OPERATING CONDITIONS
T = 230° C.
P = 6 MPa (60 bars)
VVH = 10,000 h$^{-1}$
$$\frac{H_2}{2\ CO + 3\ CO_2} = 1.2$$

What is claimed as the invention is:

1. A process for manufacturing a catalyst comprising at least, as four essential elements: copper, zinc, aluminum and at least one metal selected from the group consisting of rare earths and zirconium, characterized by the following steps of:
    (a) contacting a solution of at least one ammonium and/or alkali metal compound, selected from the group consisting of hydrogen carbonates, carbonates and hydroxides with an essentially homogeneous solution containing, as salts or soluble complexes, the assembly of copper, zinc and aluminum metals, said contact taking place at a pH ranging from 6.3 to 7.3 so as to form a precipitate, at least partly crystallized, of copper, zinc and aluminum metals, said precipitate being at least partly formed of hydroxycarbonate,
    (b) washing the precipitate obtained in step (a) with water, the obtained product having an alkali metal content reduced to less than about 0.06% by weight with respect to the total metals weight of the precipitate,
    (c) contacting a solution containing an ammonium compound selected from the group consisting of the hydrogen carbonate, carbonate and hydroxide, with a solution of a soluble salt and/or complex of at least one metal selected from the group of the rare earths and zirconium, said contact taking place at a pH from 6 to 8, so as to form a precipitate of at least one compound of metal from the group formed of rare earths and zirconium,
    (d) washing the precipitate obtained in step (c) with water so as to reduce its nitrogen content to less than 3% by weight with respect to the metals weight,
    (e) admixing the precipitate, at least partly crystallized, obtained in step b with the precipitate obtained in step (d), so as to form a substantially homogeneous dispersion,
    (f) drying and thermally activating the substantially homogeneous dispersion obtained in step (e).

2. A process for manufacturing a catalyst according to claim 1, characterized by the following steps of:
    (a) contacting a solution of at least one ammonium and/or alkali metal compound, selected from the group of the hydrogen carbonates, carbonates and hydroxides, containing a maximum of 4 gram-atoms per liter of ammonium and/or alkali metals, with an essentially homogeneous solution containing the assembly of copper, zinc and aluminum metals, as soluble salts and/or complexes, at a total concentration of at most 2 gram-atoms per liter, said contact taking place at a pH of 6.3–7.3 and at a temperature of at least 60° C., so as to form a precipitate, at least partly crystallized, of copper, zinc and aluminum metals, said precipitate being at least partly formed of hydroxycarbonate,
    (b) washing with water the at least partly crystallized precipitate of copper, zinc and aluminum metals obtained in step (a), the resultant product having an alkali metals content reduced to less than about 0.06% by weight with respect to the total metals weight of the precipitate,
    (c) contacting a solution containing an ammonium compound selected from the group formed of the hydrogen carbonate, carbonate and hydroxide with a solution of a soluble salt and/or complex of at least one metal selected from the group formed of rare earths and zirconium, said contact taking place at a pH from 6 to 8, so as to form a precipitate of at least one metal of the group formed of rare earths and zirconium, (d) washing the precipitate obtained in step (c) with water so as to reduce its nitrogen content to less than 3% by weight with respect to the metals weight, (e) admixing the at least partly crystallized precipitate obtained in step b with the precipitate obtained in step (d) so as to form a substantially homogeneous dispersion, (f) drying and thermally activating the substantially homogeneous dispersion obtained in step (e).

3. A process for manufacturing a catalyst according to claim 1, characterized in that, during step (a), the two solutions are contacted at a pH from 6.6 to 7.0, the obtained precipitate, at least partly crystallized, is washed so as to obtain a product containing less than 0.04% by weight of alkali metals with respect to the total metals weight of the precipitate; the precipitate of at least one metal selected from the group formed of rare earths and zirconium, obtained in step (c) is washed until its nitrogen content is reduced to less than 1% by weight with respect to the total metals weight; the precipitates obtained in steps (b) and (d) being admixed so as to obtain a mixture homogeneous at the scale of 0.01–0.1 micron.

4. A process according to claim 1, characterized in that, during step (a) and during step (c), the metal prrecipitates are formed from homogeneous solutions of nitrates of the considered metals and from a solution of alkali metal carbonates or hydrogen carbonates for step (a) and a solution of ammonium carbonates or hydrogen carbonates for step (c).

5. A process according to claim 1, characterized in that the catalyst further comprises at least one additional metal M selected from the group formed of palladium, silver, rhenium and platinum.

6. A process according to claim 5, characterized in that at least one additional metal selected from the group formed of palladium, silver and rhenium is introduced in step (a), as soluble compound.

7. A process according to claim 1, characterized in that at least one additional metal M selected from the group formed of palladium, silver, rhenium and platinum is introduced uniformly in the thermally activated homogeneous mixture obtained in step (f).

8. A process according to claim 7, characterized in that at least one additional metal M is introduced from salts or complexes containing no sulfur or halogen in their compositions.

9. A process according to claim 1, characterized in that, during step (a), the residence time of the precipitate, at least partly crystallized, in the reaction medium, is at least thirty minutes.

10. A catalyst obtained according to claim 5, characterized by the following percents by weight of metals, in proportion to the total metals weight:

| Copper | 20–80% |
|---|---|
| Zinc | 5–50% |
| Aluminum | 2–30% |
| Rare earths and/or zirconium | 2–20% |
| Alkali metals | 0–0.06% |
| Metal M | >0–10% |

11. A catalyst according to claim 10, characterized in that the proportions by weight of metals with respect to the total metals weight are:

| Copper | 45–70% |
|---|---|
| Zinc | 15–35% |
| Aluminum | 4–20% |
| Rare earths and/or zirconium | 5–18% |
| Alkali metals | 0–0.06% |
| Metal M | >0–0.5% |

12. Catalyst according to claim 10, characterized in that metal M is palladium, platinum or rhenium, used at a concentration of 0.01–1% by weight and/or silver at a concentration of 0.5–5% by weight.

13. A catalyst produced by the process of claim 2.
14. A catalyst produced by the process of claim 3.
15. A catalyst produced by the process of claim 4.
16. A catalyst produced by the process of claim 5.
17. A catalyst produced by the process of claim 6.
18. A catalyst produced by the process of claim 7.
19. A catalyst produced by the process of claim 8.
20. A catalyst produced by the process of claim 9.

21. A process for manufacturing a catalyst comprising at least, as four essential elements: copper, zinc, aluminum and at least one metal selected from the group consisting of rare earths and zirconium, characterized by the following steps of:

(a) contacting a solution of at least one ammonium and/or alkali metal compound, selected from the group consisting of hydrogen carbonates, carbonates and hydroxides with an essentially homogeneous solution containing, as salts or soluble complexes, the assembly of copper, zinc and aluminum metals, said contact taking place at a pH ranging from 6.3 to 7.3 so as to form a precipitate, at least partly crystallized, of copper, zinc and aluminum metals, said precipitate being at least partly formed of hydroxycarbonate, (b) washing the precipitate obtained in step (a) with water, the obtained product having an alkali metal content reduced to less than about 0.06% by weight with respect to the total metals weight of the precipitate, (c) contacting a solution containing an ammonium compound selected from the group consisting of the hydrogen carbonate, carbonate and hydroxide, with a solution of a soluble salt and/or complex of at least one metal selected from the group of the rare earths and zirconium, said contact taking place at a pH from 6 to 8, so as to form a precipitate of at least one compound of metal from the group formed of rare earths and zirconium, (d) washing the precipitate obtained in step (c) with water so as to reduce its nitrogen content to less than 3% by weight with respect to the metals weight, (e) admixing the precipitate, at least partly crystallized, obtained in step (b) with the precipitate obtained in step (d), so as to form a substantially homogeneous dispersion, (f) drying the substantially homogeneous dispersion obtained in step (e).

22. A catalyst as produced in accordance with claim 21.

* * * * *